(12) United States Patent
Kim et al.

(10) Patent No.: US 7,070,956 B2
(45) Date of Patent: Jul. 4, 2006

(54) PEPTIDES AND DERIVATIVES THEREOF SHOWING CELL ATTACHMENT, SPREADING AND DETACHMENT ACTIVITY

(75) Inventors: In-San Kim, Taegu (KR); Jung-Eun Kim, Taegu (KR)

(73) Assignee: Regen Biotech, Inc., Seoul (KR)

( * ) Notice: Subject to any disclaimer, the term of this patent is extended or adjusted under 35 U.S.C. 154(b) by 440 days.

(21) Appl. No.: 10/276,601

(22) PCT Filed: Dec. 6, 2000

(86) PCT No.: PCT/KR00/01413

§ 371 (c)(1),
(2), (4) Date: Nov. 14, 2002

(87) PCT Pub. No.: WO01/87928

PCT Pub. Date: Nov. 22, 2001

(65) Prior Publication Data

US 2003/0175885 A1    Sep. 18, 2003

(51) Int. Cl.
C12P 21/06 (2006.01)
C12N 15/00 (2006.01)
C12N 5/00 (2006.01)
C07K 1/00 (2006.01)
C07K 14/00 (2006.01)

(52) U.S. Cl. .................. 435/69.1; 435/320.1; 435/325; 530/350; 536/23.5

(58) Field of Classification Search ............... 424/93.7; 514/12
See application file for complete search history.

(56) References Cited

U.S. PATENT DOCUMENTS

| | | | | |
|---|---|---|---|---|
| 5,444,164 | A * | 8/1995 | Purchio et al. ............ | 536/23.5 |
| 2003/0175885 | A1 * | 9/2003 | Kim et al. ................. | 435/69.1 |
| 2003/0211141 | A1 * | 11/2003 | LeBaron et al. ............ | 424/450 |
| 2004/0052767 | A1 * | 3/2004 | Kim et al. ................. | 424/93.7 |

FOREIGN PATENT DOCUMENTS

WO      WO 01/57277    *  9/2001

OTHER PUBLICATIONS

J Rudinger. In: Peptide Hormones, JA Parsons, Ed. (1976) 1-7.*

SIGMA. Designing Custom Peptides. http://www.sigma-genosys.com/peptide_design.asp (Accessed Dec. 16, 2004). 2 pages.*
HJC Berendsen. A Glimpse of the Holy Grail? Science (1988) 282. 642-643.*
D Voet and JG Voet. Biochemistry. 2nd edition (1995). 235-241.*
DE Smilek et al. A single amino acid change in a myelin basic protein peptide confers the capacity to prevent rather than induce experimental autoimmune encephalomyelitis. Proc. Natl. Acd Sci. USA (1991) 88. 9633-9637.*
Skonier et al. cDNA Cloning and Sequence Analysis of Big-h3, a Novel Gene Induced in a Human Adenocarcinoma Cell Line after Treatment with Transforming Growth Factor-B. DNA Cell Biol. (1992). 11(7), 511-522.*
Cole et al. Deciphering the biology of *Mycobacterium tuberculosis* from the complete genome sequence. Nature. (1998). 393. pp. 537-544 and 10 additional pages for Table 1.*
Cole et al. Deciphering the biology of *Mycobacterium tuberculosis* from the complete genome sequence (Errata). Nature. (1998) 396. pp. 190-198.*
Definition of represent. http://www.answers.com/represent &r=67 (accessed online Nov. 7, 2005), 1 page.*
Kim et al., J. Biol. Chem. 2000, vol. 275, No. 40, pp. 30907-30915.
Goldberg et al., J. Biol. Chem. 2000, vol. 275, No. 32, pp. 24622-24629.
Skonier et al., DNA Cell Biol. 1994, vol. 13, No. 6, pp. 571-584.
Tom et al., Nature 1997, vol. 388, pp. 539-547.

* cited by examiner

Primary Examiner—Bruce Campell
Assistant Examiner—Marcela M Cordero Garcia
(74) Attorney, Agent, or Firm—JHK Law; Joseph Hyosuk Kim

(57) ABSTRACT

The present invention relates to peptides and derivatives thereof showing cell attachment, spreading and detachment activity. Particularly, the present invention relates to the peptide NKDIL and EPDIM and derivatives thereof which promote the cell attachment activity through interaction with a α3β1 integrin as a functional cell receptor and include aspartic acid and isoleucine essential for cell attachment and detachment activity. The peptides and derivatives thereof in the present invention can be used for developing a study of cell attachment activity mediated through various extracellular matrix protein containing β ig-h3, wound healing, tissue regeneration and metastasis inhibition.

9 Claims, 15 Drawing Sheets

FIG. 4

|  |  | H2 |  |
|---|---|---|---|
| BIGH3_HUMAN | 211 | TVNCARLLKADHHATNGVVHLIDKVI... | 236 |
| BIGH3_PIG | 211 | TVNCARLLKADHHATNGVVHLIDKVI... | 236 |
| BIGH3_CHICK | 201 | TVNCARLLKADHHATNGVVHVIDKVI... | 228 |
| BIGH3_HUMAN | 346 | INGKAIISNKDILATNGVIHYIDELLI.. | 372 |
| BIGH3_PIG | 346 | INGKPIISNKDVLATNGVIHFIDELLI,. | 372 |
| BIGH3_CHICK | 338 | LNGRAIIANKDILATNGVVHFVNELLI.. | 364 |
| OSF2_HUMAN | 340 | VNGIKMVNKKDIVTNNGVIHLIDQVLI.. | 366 |
| OSF2_MOUSE | 342 | INGIKMVNKKDIVTKNGVIHLIDEVLI.. | 368 |
| BIGH3_HUMAN | 608 | VNKEPVAE-PDIMATNGVVHVITNVL... | 632 |
| BIGH3_PIG | 608 | VNKEPVAE-ADIMATNGVVHTINTVL... | 632 |
| BIGH3_CHICK | 600 | VNKEPVAE-SDIMATNGVIHAVSSVL... | 624 |
| SLL1735 homolog | 106 | VKNATVLA-ADIEADNGIIHVIDNVILMG | 133 |
| SLL1735 | 106 | VKNATVII-PDIEADNGIIHVIDNVILMG | 133 |
| SLL1483 | 152 | VNKATVIS-ADVDASNGVIHVIDQVIL.. | 177 |
| OSF2_HUMAN | 604 | VNELKSKE-SDIMTTNGVIHVVDKLL... | 628 |
| OSF2 MOUSE | 606 | VNELKSKE-SDIMTTNGVIHVVDKLL... | 630 |
| Midline Fasciclin | 543 | INNLAKIIDADIMGTNGVLHVIDTIL... | 568 |
| HLC-32 | 341 | -SKASRVILRDIPTTNGVIQVIDRVIL.. | 366 |
| Midline Fasciclin | 825 | KIENAGVTKCDVVATNGILHEINDIIV.. | 851 |
| HLC-32 | 196 | TANGARVVEADRKASSGLIHVVDKVI... | 221 |
| consensus |  | VNNAARVVKADIHATNGVIHVIDKVLIMG |  |

FIG. 7

```
                     219   223
βigh3 D-I    133 ----GIVTVNCARLLKADHHATNGVVHLIDKVI... 236

354   358
βigh3 D-II   242 ----MLTINGKAIISNKDILATNGVIHYIDELLI.. 372

615   619
βigh3 D-IV   501 ----GVVSVNKEPVAEPDIMATNGVVHVITNVL... 632

Control                       DEMPI
```

PEPTIDES AND DERIVATIVES THEREOF SHOWING CELL ATTACHMENT, SPREADING AND DETACHMENT ACTIVITY

CONTINUING DATA

The present application is a U.S. national phase application under 35 U.S.C. §371, of PCT/KR00/01413, filed Dec. 6, 2000.

FIELD OF THE INVENTION

The present invention relates to peptides and derivatives thereof showing cell attachment, spreading and detachment activity. Particularly, the present invention relates to the peptide NKDIL and EPDIM and derivatives thereof which promote the cell attachment activity through interaction with α3β1 integrin as a functional cell receptor and include aspartic acid and isoleucine essential for cell attachment and detachment activity.

BACKGROUND OF THE INVENTION

βig-h3 is an extracellular matrix protein whose expression is induced in various cell lines, including human melanoma cells, mammary ephithelial cells, keratinocytes, and lung fibroblasts, following signaling by active TGF-β. The βig-h3 gene was first isolated by differential hybridization screening of a cDNA library made from a human lung adenocarcima cell line that had been treated with TGF-β. βig-h3 gene encodes a 683-amino acid protein that is highly conserved between species. It contains an N-terminal secretory signal peptide and an Arg-Gly-Asp (RGD) motif at the C-terminus. The RGD motif, which modulates cell adhesion, is found in many extracellular matrix proteins and serves as a ligand recognition sequence for several integrins.

Because the expression of βig-h3 gene is increased by TGF-β in various cell lines and the gene is induced in various cell lines whose proliferation rate is controlled by TGF-β, βig-h3 is believed to be involved in mediating some of the signaling pathways of TGF-β. In contrast, βig-h3 expression is reported to be reduced in the fibroblasts cultured from the skin lesions afflicted with localized hyperostosis of melorheostosis, some tumor cells, and dexamethasone-treated stem cells. Accordingly, βig-h3 plays an important role in the morphogenesis and interactions with cells and other extracellular matrix proteins in various tissues.

Additionally, βig-h3 is known to mediate cell attachment and detachment, serving as a cell adhesion molecule. Purified βig-h3 protein is found to promote the attachment and spreading of skin fibroblasts while inhibiting the adhesion of A549, HeLa and Wi-38 cells in serum-free media. Particularly, βig-h3 is known to have inhibitory activity against tumor cell growth, and colony formation. In fact, it was reported that βig-h3 remarkably suppressed the growth of CHO (Chinese hamster ovary) cells in nude mice. Furthermore, a wound healing method was developed on the basis of the finding that application of a pharmaceutically effective amount of βig-h3 to wounds makes cells, especially fibroblasts, spread over and adhere to the wounded site. Consequently, βig-h3, a cell adhesion molecule induced by TGF-β in various cell lines, plays a very important roles in cell growth, cell differentiation, wound healing, morphogenesis and cell adhesion.

βig-h3 contains four 140 amino acid repeats with internal homology. The internally repeated domains have highly conserved sequences found in secretory proteins or membrane proteins of various species, including mammals, insects, sea urchin, plants, yeast and bacteria. Proteins such as periostin, fasciclin I, sea urchin HLC-2, algal-CAM and mycobacterium MPB70 are examples containing the conserved sequences. The homology domain conserved in these proteins (hereinafter referred to as "fas-1") consists of about 110 to 140 amino acids with two highly conserved branches of H1 and H2 which have about 10 amino acids each. Four fas-1 domains are found in βig-h3, periostin, and fasciclin I, two fas-1 domains in HLC-2, and only one fas-1 domain in MPB70. Although the functions of the proteins are not elucidated clearly, some of them are known to act as cell adhesion molecules. For instance, βig-h3, periostin, and fasciclin 1 are reported to mediate the adhesion of fibroblasts, osteoblasts, and nerve cells, respectively. Also, it is disclosed that the algal-CAM is a cell adhesion molecule present in embryos of algae Volvox.

The cell attachment activity of βig-h3 was found first in human dermal fibroblasts and then in chondrocytes, peritoneal fibroblasts and human MRC5 fibroblast. At first, it was believed that the cell attachment activity of βig-h3 would be mediated by the C-terminal RGD motif. However, some research results revealed that the RGD motif is not necessary for promoting the spread of chondrocytes and that the mature soluble βig-h3 whose RGD motif is deleted by carboxyl-terminus processing is able to inhibit cell adhesion, leading to the conclusion that the RGD motif of βig-h3 is dispensable for mediating the cell attachment activity of βig-h3. In addition, it has been recently reported that βig-h3 promotes the spread of fibroblasts via integrin α1β1 whereas the RGD motif of βig-h3 is not necessary for βig-h3-mediated cell spreading. Further, the conserved peptides H1 and H2 of βig-h3 do not inhibit βig-h3-mediated cell adhesion, so that the conserved peptides are not effective for βig-h3-mediated cell attachment. These results, taken together, indicate that amino acids indispensable for the cell attachment activity of βig-h3 exist in regions other than H1 and H2. A computer analysis of the homology among fas-1 domains of other proteins as well as between repeated fas-1 domains of βig-h3 discloses the existence of several highly conserved amino acid sequences in addition to H1 and H2 peptides, suggesting the posibility of the involvement of the conserved amino acid sequences in the cell attachment activity.

SUMMARY OF THE INVENTION

Leading to the present invention, the intensive and thorough research on conserved motifs responsible for the cell attachment and detachment activity, conducted by the present inventors, resulted in the finding that aspartic acid and isoleucine at positions near the H2 region within each of the $2^{nd}$ and $4^{th}$ fas-1 domains of βig-h3 are very highly conserved and are identified as a functionally essential unit for mediating cell adhesion through α3β1 integrin.

Therefore, it is an object of the present invention to provide peptides and their derivatives, which contain conserved amino acid sequences essential for cell attachment, spreading and detachment activity.

It is another object of the present invention to provide a pharmaceutical compositions for use in wound healing, tissue regeneration and cancer metastasis resistance.

In accordance with one embodiment of the present invention, there is provided a peptide having cell attachment, spreading and detachment activity, comprising an amino acid sequence represented by the following one-letter symbols: XXDIX wherein X is any of the twenty common amino acids, D stands for aspartic acid, and I stands for isoleucine, and derivatives thereof.

In accordance with another aspect of the present invention, there is provided a pharmaceutical composition, comprising the above peptide or its derivative as a pharmaceutically active ingredient.

BRIEF DESCRIPTION OF THE DRAWINGS

FIG. 4 shows amino acid sequences of various matrix proteins containing fas-1 domains.

FIG. 7 shows amino acid sequences of the synthetic peptides of the present invention.

DETAILED DESCRIPTION OF THE INVENTION

In the present invention, the amino acid sequence of βig-h3, known to mediate cell attachment activity, is utilized to prepare peptides comprising conserved sequences essential to cell attachment and spreading activity, based on the finding that not only βig-h3 comprising 4 fas-1 domains, but also either the $2^{nd}$ domain or the $4^{th}$ domain alone can mediate the cell attachment activity.

Figure 1A:
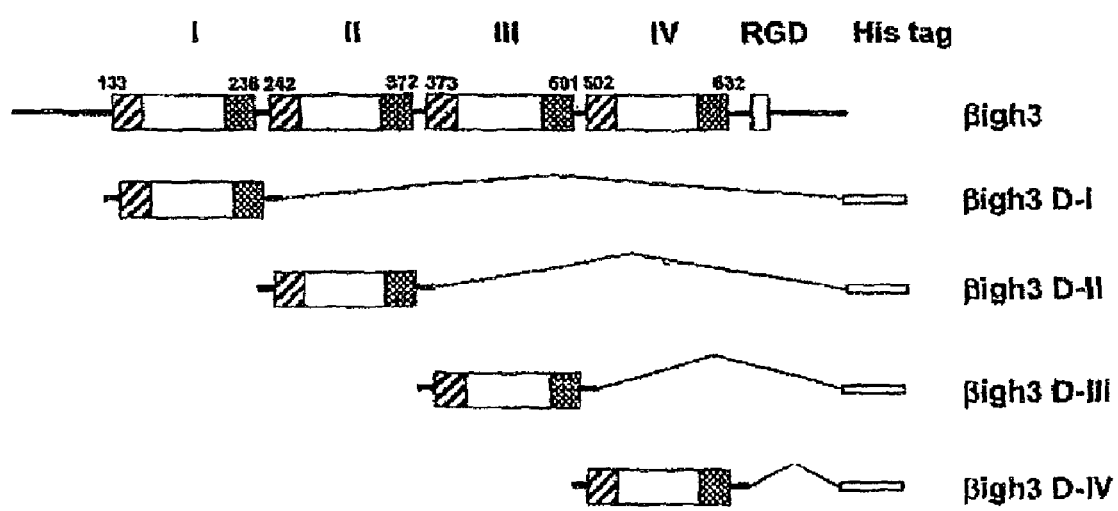
FIG. 1a is a schematic diagram showing recombinant proteins derived from fas-1 domains of βig-h3.
Figure 2:
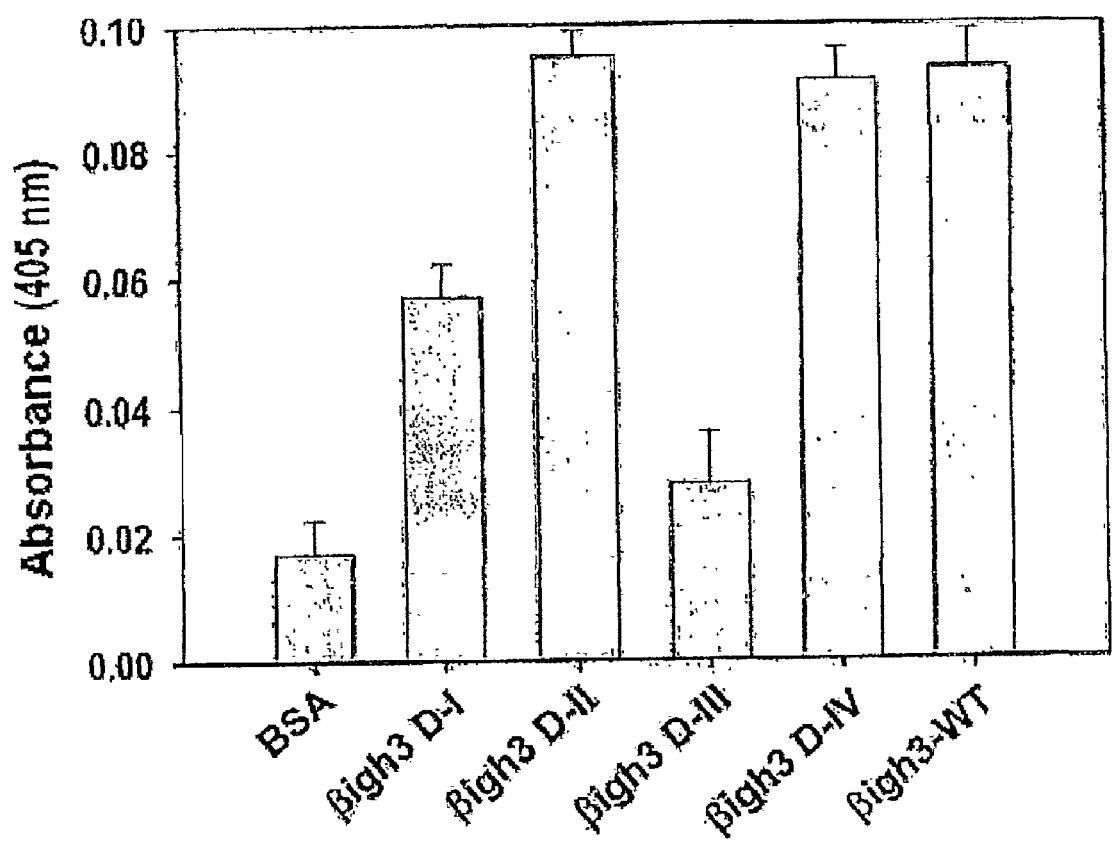
FIG. 2 is a histogram showing cell attachment activity of the recombinant proteins derived from fas-1 domains of βig-h3.

In more detail, four different truncated DNA fragments of the βig-h3 gene, that is, βig-h3 D-I, βig-h3 D-II, βig-h3 D-III, and βig-h3 D-IV, which encode $1^{st}$ to $4^{th}$ internal repeat domains, respectively, were synthesized as shown in FIG. 1a. A quantitative measurement which shows the cell attachment and spreading activity of the resulting four recombinant proteins demonstrates that only either the $2^{nd}$ or $4^{th}$ domain of the four fas-1 domains can mediate the cell attachment and spreading activity of βig-h3, as shown in FIG. 2, indicating the existence of amino acids essential to the mediation of the cell attachment and spreading in the two domains. In contrast, the $1^{st}$ domain of βig-h3 shows intermediate cell attachment and spreading activity while no cell attachment activity is found in the $3^{rd}$ domain.

Also, in accordance with the present invention, α3β1 integrin is identified as the functional receptor for the $2^{nd}$ and $4^{th}$ domains of βig-h3.

Figure 3:
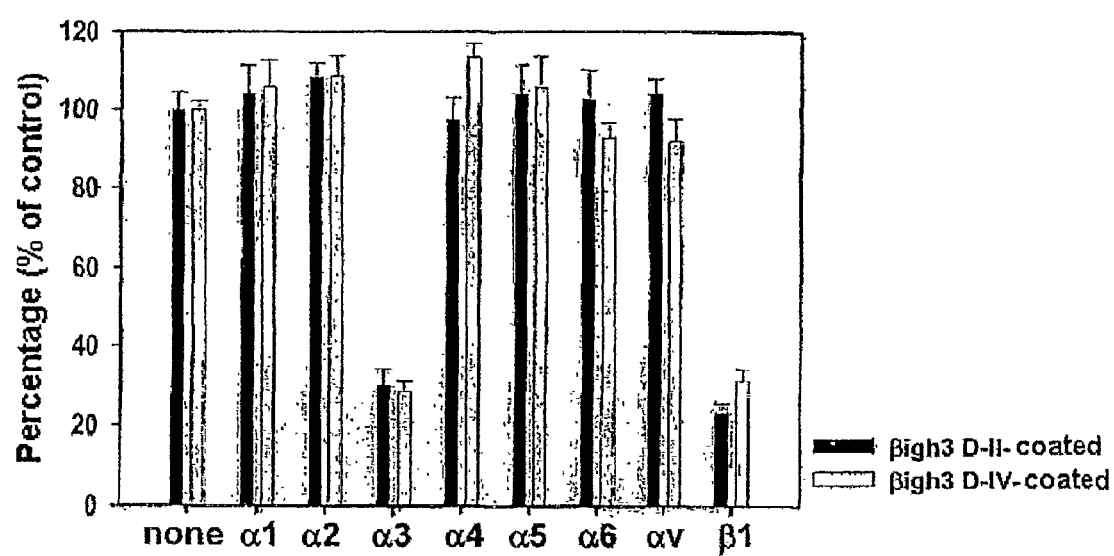
FIG. 3 is a histogram showing the inhibitory activity of anti-integrin antibody against the cell attachment activity of the recombinant proteins derived from fas-1 domains of βig-h3.

Using the truncated proteins comprising the $2^{nd}$ and $4^{th}$ domains of βig-h3, each of which shows cell attachment, spreading and detachment activity, the present inventors examined the receptors of βig-h3. The $2^{nd}$ or $4^{th}$ fas-1 domain-mediated cell attachment activity was almost completely suppressed by antibodies against α3 and β1 integrin subunits, as shown in FIG. 3. These results mean that both of the $2^{nd}$ and $4^{th}$ fas-1 domain bind to the functional receptor α3β1 integrin to mediate the cell attachment activity, and have amino acids essential to mediate cell adhesion activity.

The present invention also provides peptides which comprise the characteristic conserved amino acid sequence Asp-Ile essential to the cell attachment, spreading and detachment activity of βig-h3 and thus showing the same activity as that of the $2^{nd}$ and $4^{th}$ domains.

To find out amino acid sequence responsible for cell adhesion in the $2^{nd}$ and $4^{th}$ fas-1 domains of βig-h3, which shows cell attachment, spreading and detachment activity independently, amino acid sequence alignment was done not only among the internally repeated fas-1 domains of βig-h3, but also among other proteins containing fas-1 domains. After that, the present inventors found out that two amino acids, aspartic acid and isoleucine, near the H2 region are highly conserved between various proteins, as shown in FIG. 4.

Figure 5A:
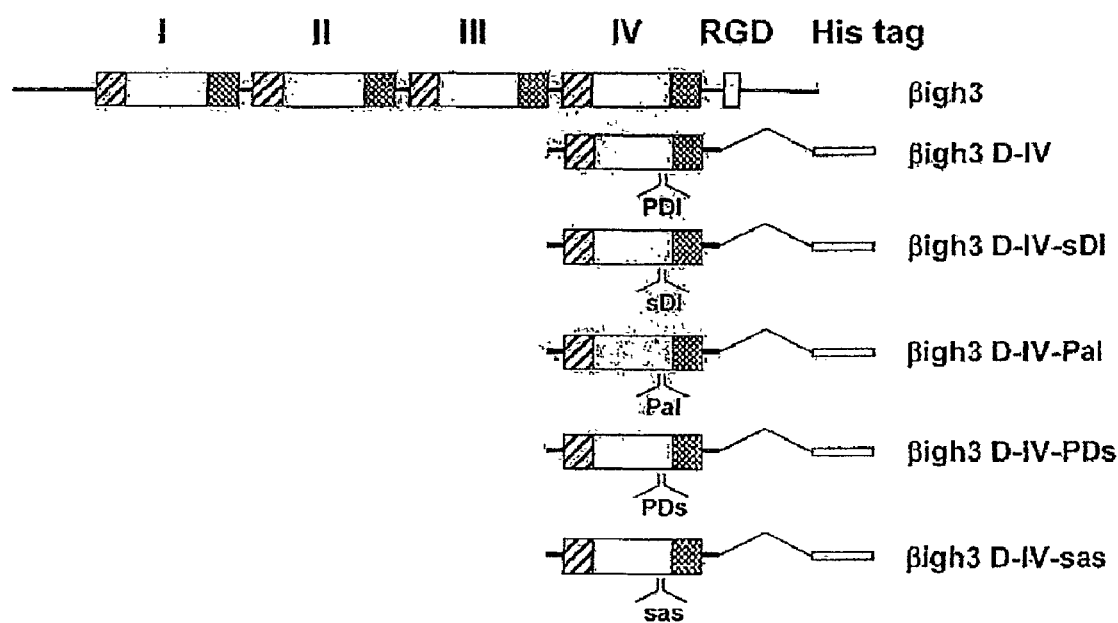
FIG. 5a is a schematic diagram showing substitution mutants derived form the $4^{th}$ fas-1 domain of βig-h3.

Next, the indispensability of the amino acid sequence aspartic acid and isoleucine to the cell attachment activity remains to be confirmed. In this regard, the truncated protein containing the $4^{th}$ fas-1 domain of βig-h3 was mutated by the substitution of proline, aspartic acid and isoleucine with serine, alanine and serine, respectively, as shown in FIG. 5a. Almost complete suppression of the $4^{th}$ fas-1 domain-mediated cell attachment activity was observed in the mutant proteins in which aspartic acid and isoleucine were substituted, confirming that the amino acid sequence aspartic acid and isoleucine is very important in mediating the cell attachment activity of βig-h3.

In addition, aspartic acid and isoleucine are both conserved in the $2^{nd}$ and $4^{th}$ fas-1 domains of βig-h3, which are of high cell attachment activity, while only aspartic acid is conserved in the $1^{st}$ fas-1 domain 1, which shows intermediate cell attachment activity. As for the $3^{rd}$ fas-1 domain which shows no cell attachment activity, it has neither of the two amino acids. Those facts are further evidence showing that aspartic acid and isoleucine are indispensable to mediate cell attachment and spreading activity.

With the confirmation of the indispensability of aspartic acid and isoleucine for cell attachment activity, three peptides containing the two amino acids were synthesized from fas-1 domains I, II and IV of βig-h3, respectively. These peptides have the conserved sequences of the fas-1 domains I, II and IV of βig-h3. That is, the peptides are designed to have KADHH (a.a. 219–223) of SEQ. ID. NO. 1, NKDIL (a.a. 354–358) of SEQ. ID. NO. 2, and EPDIM (a.a. 615–619) of SEQ. ID. NO. 3, as shown in FIG. 7.

Figure 8A:
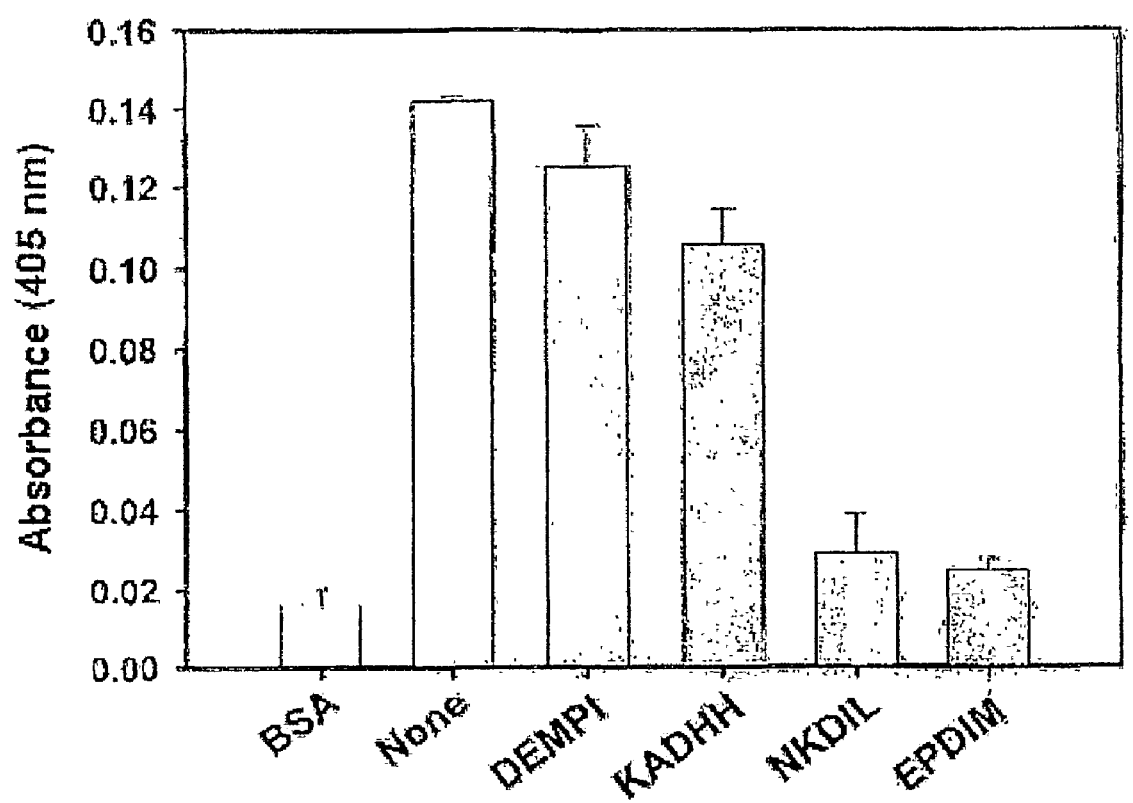
FIG. 8a is a histogram showing the inhibitory activity of the synthetic peptides against HCE cell adhesion.
Figure 8B:
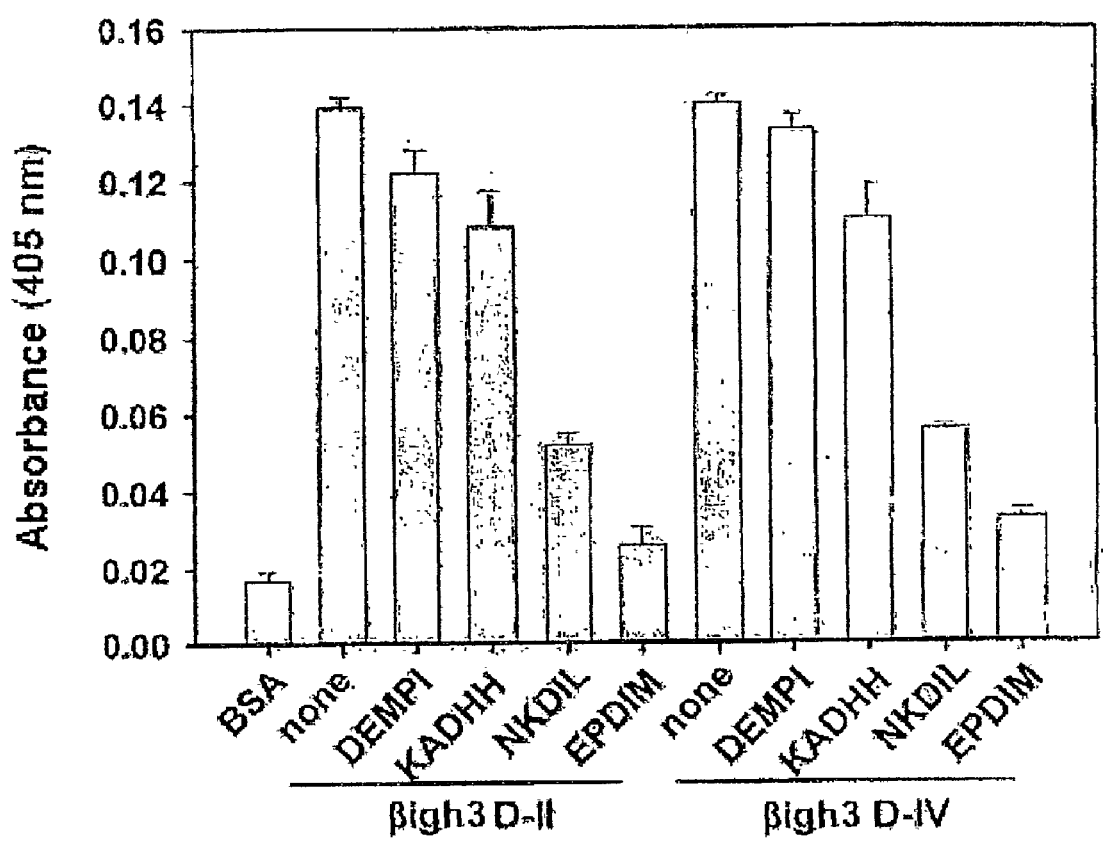
FIG. 8b is a histogram showing inhibition of HCE cell adhesion to βig-h3 D-II or βig-h3 D-IV proteins by the synthetic βig-h3 peptides.

As a matter of course, these synthetic peptides derived from the fas-1 domains of βig-h3 were examined for cell attachment and detachment activity. The $2^{nd}$ fas-1 domain-derived synthetic peptide NKDIL and the $4^{th}$ fas-1 domain-derived synthetic peptide EPDIM were measured to show very excellent cell detachment effect with significant suppression of the cell attachment activity, as seen in FIG. 8a. On the other hand, relatively very low cell detachment effects were observed in the $1^{st}$ fas-1 domain-derived synthetic peptide KADHH owing to its weak suppression of cell adhesion, and also the control peptide DEMPI failed to show, owing to its deficiency in cell adhesion activity. The suppression effects against the cell attachment activity obtained when using the $2^{nd}$ and $4^{th}$ fas-1 domains as substrates were almost the same as those obtained when using βig-h3 as a substrate, as shown in FIG. 8b.

Figure 9A:
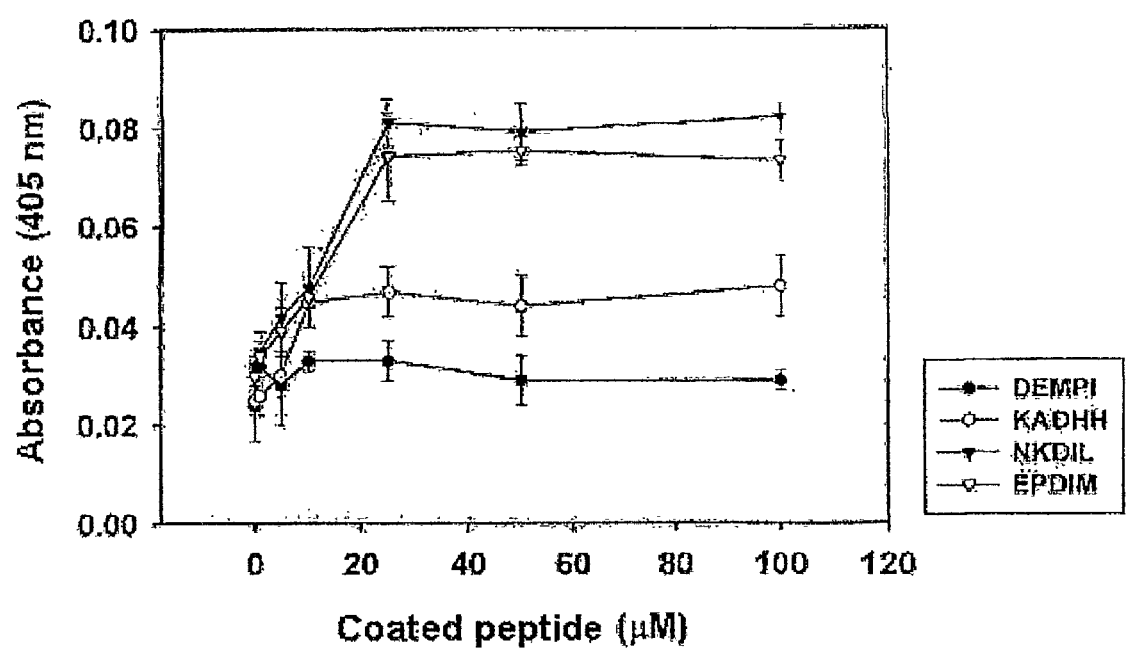
FIG. 9a is a curve showing HCE cell attachment activity according to the synthetic peptides of the present invention.
Figure 9B:
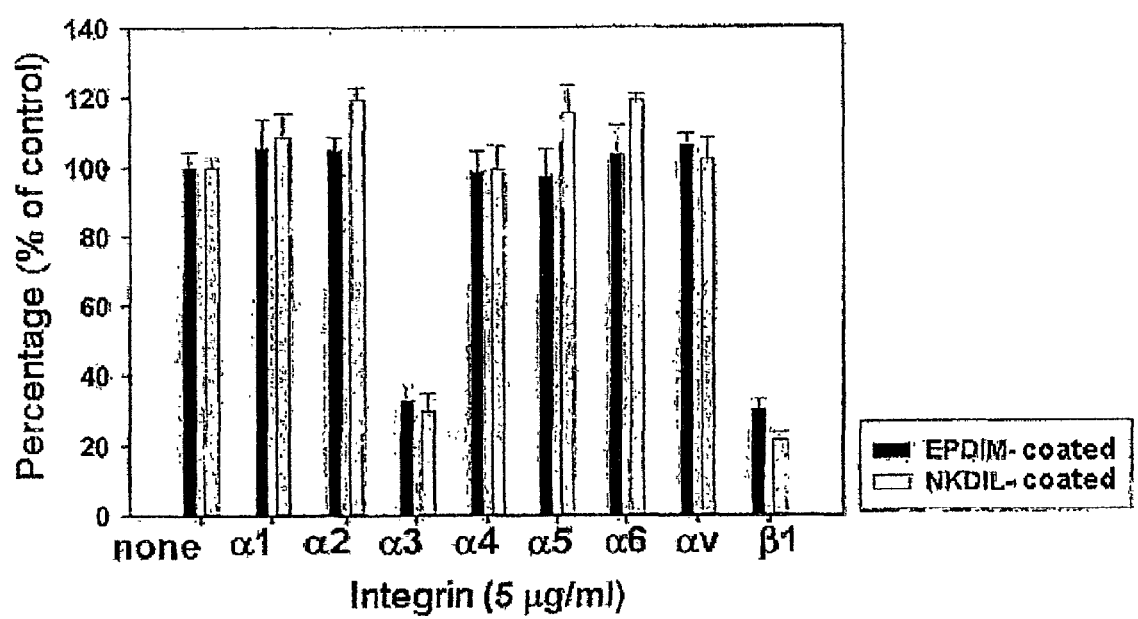
FIG. 9b is a histogram showing the inhibition of anti-integrin antibodies against HCE cell adhesion to the synthetic peptides EPDIM and NKDIL.
Figure 10A:
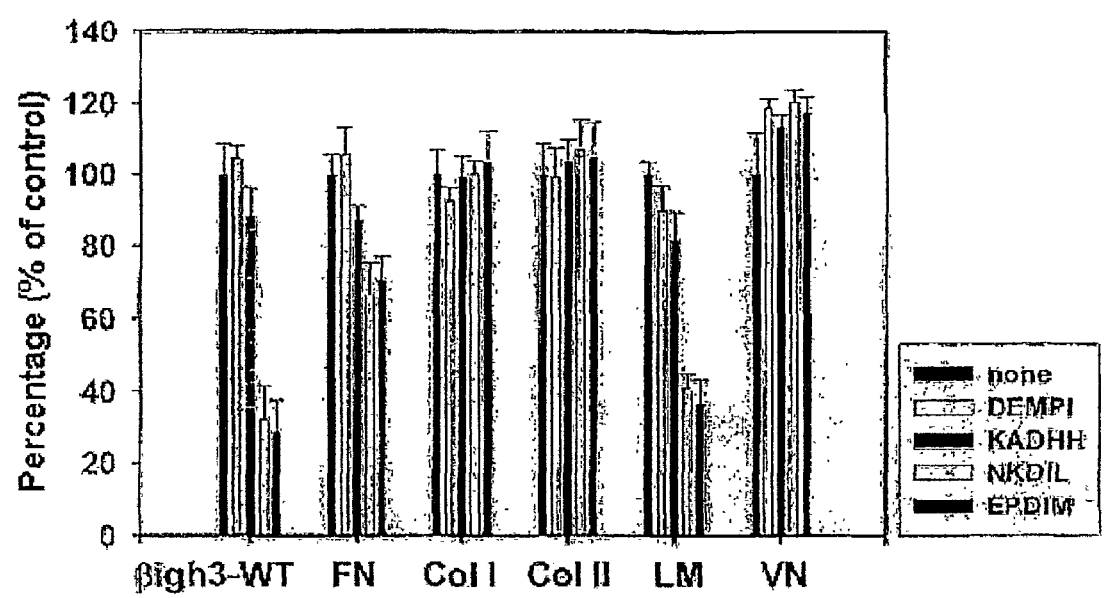
FIG. 10a is a histogram showing effects of the synthetic peptides of the present invention on HCE cell adhesion to several extracellular matrix proteins.

As shown in FIG. 9a, the synthetic peptides NKDIL and EPDIM are capable of mediating cell adhesion in dose-dependent manners. Moreover, the α3β1 integrin, known as a surface receptor of βig-h3, was revealed to act as a receptor in the synthetic peptides EPDIM and NKDIL-mediated cell adhesion, as seen in FIG. 9b. For these reasons, NKDIL and EPDIM appeared to specifically compete with α3β1-interacting molecules, as shown in FIG. 10a.

In the present invention, as described above, there are provided the peptides, NKDIL and EPDIM, which contain aspartic acid and isoleucine essential to the cell attachment and detachment activity, and are sufficient to induce cell adhesion through α3β1 integrin, which is the functional receptor for βig-h3. These peptide sequences are derived from the conserved sequence of the fas-1 domains II and IV, which independently induces cell adhesion. The peptides of the present invention can be used usefully for studying the cell attachment activity mediated through various extracellular matrix proteins, including βig-h3, and developing cell attachment, spreading and detachment-promoting peptides.

In accordance with a further aspect of the present invention, there are provided pharmaceutical compositions comprising the peptides showing cell attachment and detachment activity or their derivatives as effective ingredients conferring wound healing and tissue regeneration ability and resistance to cancer metastasis.

Administrable via oral or parenteral routes, the peptides or their derivatives may be used with ordinary medicine forms. That is, the peptides or their derivatives can be formulated into various dosage forms for parenteral administration. For formulation, pharmaceutically acceptable diluents, expedients and/or carriers may be used, including fillers, thickeners, binders, wetting agents, disintegrants, surfactants, etc. Dosage forms for parenteral administration include sterile aqueous solutions, non-aqueous solvents, suspensions, emulsions, freeze-dried agents, suppositories, etc. For formulation of non-aqueous solvents and suspensions, vegetable oils, such as propylene glycol and polyethylene glycol, or injectable esters such as ethyl oleate, may be used. As bases for suppositories, Witepsol, macrogol, Tween 61, cocoa butter, laurinic acid, and glycerogelatine are useful.

In addition, the peptides and their derivatives may be used in combination with pharmaceutically acceptable carriers such as biologically active saline or organic solvents. Also, carbohydrates such as glucose, sucrose, and dextran, antioxidants such as ascorbic acid and glutathion, chelating agents, low molecular weight proteins, or other stabilizers may be employed to increase the stability or absorption of the peptides.

The total effective amount of the peptides may be administered as a dosage form of a bolus or may be administered by infusion in a single dose when a relatively short period of administration is desired. Alternatively, the administration of the peptides may follow a multiple-dose manner according to a fractionated treatment protocol. Depending on the ages, body conditions and body weights of the patients as well as administration routes and treatment number, the pharmaceutically effective dosage of the peptides of the present invention may be varied, and can be easily determined by those skilled in the art.

Because the pharmaceutical compositions comprising the peptides or their derivatives as therapeutically effective ingredients are administered parenterally, they were not tested for toxicity.

EXAMPLES

A better understanding of the present invention may be obtained in light of the following examples which are set forth to illustrate, but are not to be construed to limit the present invention.

Example 1

Generation of Recombinant βig-h3 Fas-1 Domain Proteins and Assay for Cell Attachment Activity To find the amino acids essential to the cell adhesion of βig-h3, the ability of each of the four repeat fas-1 domains to mediate the cell adhesion of βig-h3 was examined. To this end, four recombinant proteins that contained the four repeat fas-1 domains respectively were generated for cell attachment activity assay.

1-1 Production of Recombinant βig-h3 fas-1 Proteins Encoding Each of Four Repeat Domains Four DNA fragments encoding the $1^{st}$ to $4^{th}$ domains corresponding to the amino acid residues 133 to 236, 242 to 372, 373 to 501, and 501 to 632 of the human βig-h3 protein, respectively, were generated by PCR and cloned into pET-29β(Novagen) to construct expression vectors for fas-1 domains, named βig-h3 D-I, βig-h3 D-II, βig-h3 D-III, and βig-h3 D-IV, as shown in FIG. 1a. 6 tandem repeated histidine residues were provided to the C-termini of the DNA fragments to make a His-tag, which is useful for the purification of the expressed proteins by use of Ni-NTA resin (Quiagen). E. coli strain BS21(DE3,) was transformed with each of the recombinant expression vectors and cultured in LB media containing 50 μg/ml kanamycin. The recombinant βig-h3 proteins were induced by culturing the transformants in the presence of 1 mM IPTG, followed by centrifugation. The pellet was suspended in a lysis buffer consisting of 50 mM Tris-HCl (pH 8.0), 100 mM EDTA, 1% Triton X-100, 1 mM PMSF and 0.5 mM DTT and then sonicated to lyse the cells. After five repetitions of the procedure, centrifugation was conducted to separate a supernatant from which the proteins of interest were purified through a column filled with Ni-NTA resin.

Figure 1B:
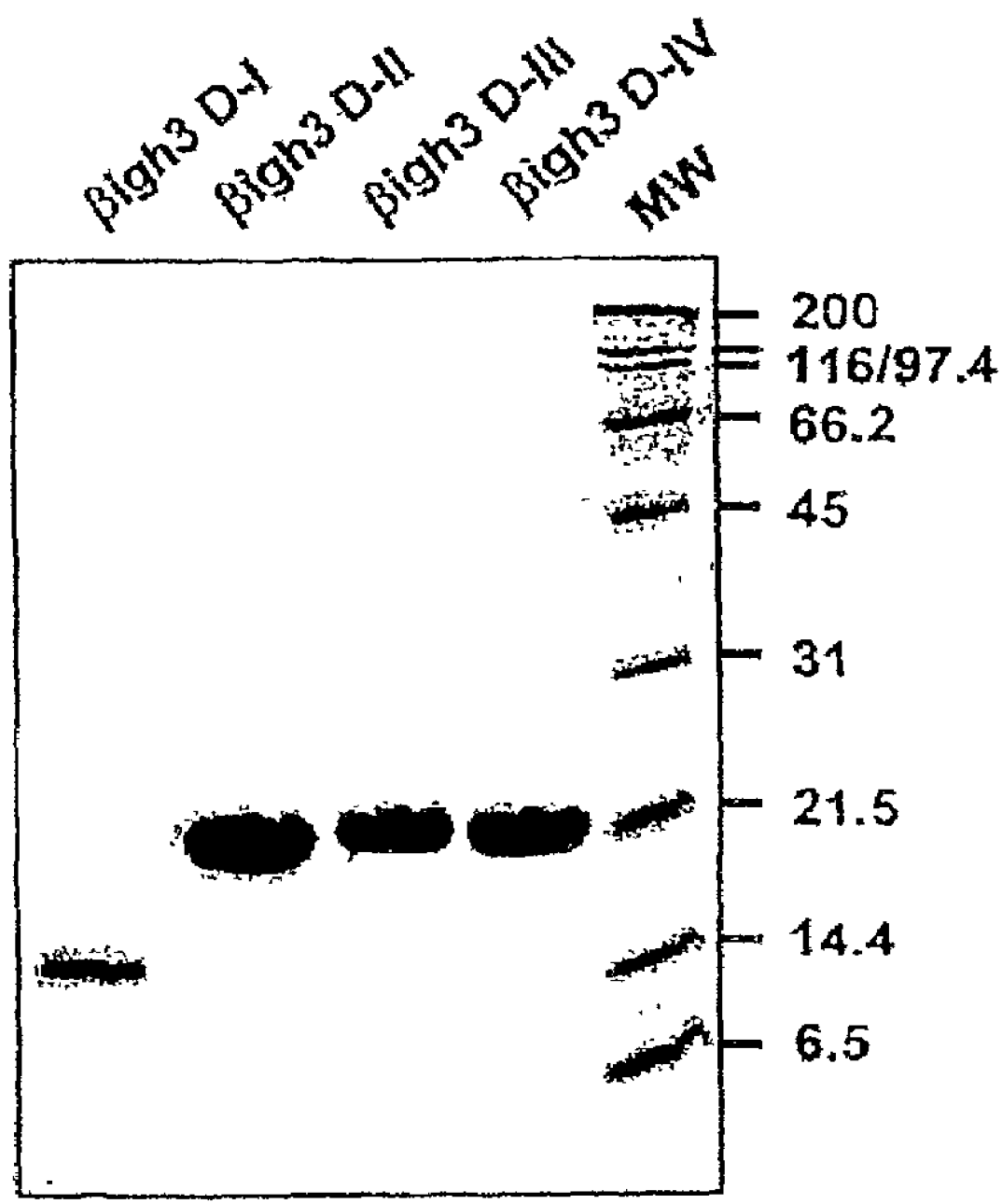
FIG. 1b is a photograph showing SDS-PAGE results of the recombinant proteins derived from fas-1 domains of βig-h3.

On SDS-PAGE, the recombinant protein βig-h3 D-I was detected at 14.4 Kda, while all of the recombinant proteins βig-h3 D-II, βig-h3 D-III, and βig-h3 D-IV were detected at 21.5 KDa, as shown in FIG. 1b.

1-2: Assay for the Cell Attachment Activity of Recombinant βig-h3 fas-1 Domain Proteins The recombinant βig-h3 fas-1 domain proteins prepared above were assayed for cell attachment activity. First, the recombinant βig-h3 proteins were let to adhere to the bottoms of 96-well microculture plates (Falcon) by incubation at 37° C. for 1 hour and blocked with PBS containing 0.2% BSA. HCE cells were suspended in culture media at a density of $2 \times 10^5$ cells/ml. 0.1 ml of the cell suspension was added to each well of the plates coated with the recombinant proteins. Following incubation at 37° C. for 1 hour, unattached cells were removed by washing with PBS. Attached cells were incubated for 1 hour at 37° C. in 50 mM citrate buffer, pH 5.0, containing 3.75 mM p-nitrophenol-N-acetyl 1-β-D-glycosaminide as a hexosaminidase substrate and 0.25% Triton X-100, followed by the addition of 50 mM glycine buffer, pH 10.4, containing 5 mM EDTA to block the enzyme activity. A measurement was made of absorbance at 405 nm in a Multiskan MCC/340 microplate reader. Absorbance results are shown in FIG. 2.

As seen in the histogram of FIG. 2, HCE cells showed cell attachment and spreading activity comparable to the activity of wild type βig-h3 (βig-h3-WT) in both plates coated with the recombinant $2^{nd}$ fas-1 domain protein (βigh3-D-II) and recombinant $4^{th}$ fas-1 domain protein (β igh3-D-IV) while exhibiting weak activity in the plate coated with the recombinant $1^{st}$ fas-1 domain protein (β igh3-D-I). On the other hand, almost no activity was detected in the plate coated with the recombinant fas-1 domain III protein (β igh3-D-III).

Either the $2^{nd}$ or $4^{th}$ fas-1 domain is sufficient to mediate cell adhesion and spreading, indicating that amino acids essential to cell adhesion and spreading are present in each of the two domains.

1-3: Identification of Receptors for βig-h3 fas-1 Domain Proteins

Using the recombinant βig-h3 $2^{nd}$ and $4^{th}$ domain proteins, each showing cell attachment and spreading activity, βig-h3 receptors were examined. In this regard, effects of function-blocking monoclonal antibodies against various integrin subunits on the adhesion of HCE cells to a surface coated with βig-h3 were examined.

In detail, HCE was preincubated in an incubation solution ($3 \times 10^5$ cells/ml) in the presence of each of the monoclonal antibodies (5 μg/ml) against different types of integrins at 37° C. for 30 min. The preincubated cells were transferred onto plates precoated with βig-h3 proteins and then incubated further at 37° C. for 1 hour, followed by the quantitative analysis with hexosaminidase substrate as described in Example 1–2. The quantitative results are given in FIG. 3, in which the values are expressed as percentages of the number of cells adhering in the absence of monoclonal antibodies.

As seen in FIG. 3, the $2^{nd}$ or $4^{th}$ fas-1 domain-mediated cell adhesion was almost completely inhibited by both antibodies against α3 and β1 integrin subunits. These results indicate that both the $2^{nd}$ and $4^{th}$ fas-1 domains are associated with α3β1 integrin to mediate the cell attachment activity and have amino acids essential to the mediation.

Example 2

Amino Acids, Aspartic Acid and Isoleucine, Essential to the Cell Attachment and Spreading Activity of βig-h3

2-1: Amino Acid Sequence Alignment of Various Proteins Containing fas-1 Domains To identify amino acids responsible for cell adhesion from $2^{nd}$ and $4^{th}$ fas-1 domains of βig-h3, each having cell attachment and spreading activity, not only the internal repeat fas-1 domains of βig-h3, but also other proteins containing fas-1 domains were subjected to amino acid sequence alignment. As a result, two amino acids, that is, aspartic acid and isoleucine were found to be highly conserved at the site near the H2 region of each fas-1 domain among various substrate proteins, as shown in FIG. 4. On the whole, both aspartic acid and isoleucine are conserved in various fas-1 domains, including the $2^{nd}$ and $4^{th}$ fas-1 domains of βig-h3, while only aspartic acid is conserved in the $1^{st}$ fas-1 domain. As for the $3^{rd}$ fas-1 domain, it has neither of the two amino acids.

2-2: Generation of Recombinant Proteins Containing Substitution Mutants of the $4^{th}$ fas-1 Domain of βig-h3

Figure 5B:
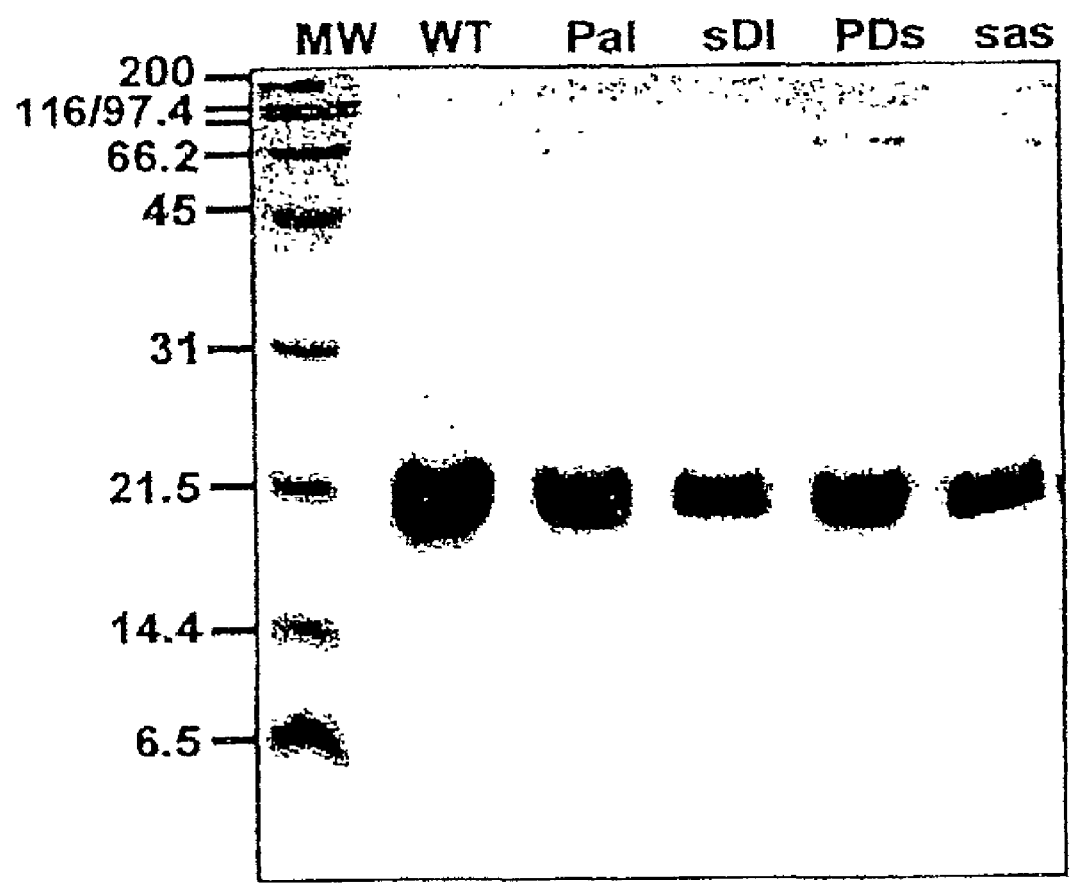
FIG. 5b is a photograph showing 15% polyacrylamide gel electrophoresis results of substitution mutants derived from the $4^{th}$ fas-1 domain of βig-h3.

In order to examine the essentiality of aspartic acid and isoleucine to the cell adhesion activity of βig-h3, mutants of the recombinant protein βig-h3 D-IV derived from the $4^{th}$ domain of βig-h3 were generated in which serine, alanine, and serine were substituted for proline at position 616, aspartic acid at position 617, and isoleucine at position 618, respectively. The resulting mutated recombinant proteins were designated βigh3 D-IV-sDI, βigh3 D-IV-PaI, βigh3 D-IV-PDs, and βigh3 D-IV-sas (FIG. 5a). On SDS-PAGE, all of the mutated recombinant proteins were detected at the same position as that of βigh3 D-IV (FIG. 5b).

2-3: Assay for Cell Attachment Activity of Recombinant Proteins Containing Substitution Mutants of the $4^{th}$ fas-1 Domain of βig-h3

Examination was made of the cell attachment activity of the mutated proteins wherein the Pro616, Asp617 and Ile618 of βigh3 D-IV were substituted, in combination, with Ser, Ala and Ser, respectively, that is, β igh3 D-IV-sDI, β igh3 D-IV-PaI, β igh3 D-IV-PDs, and β igh3 D-IV-sas. To this end, HCE cells were incubated at 37° C. for 1 hour in well plates coated with the mutant proteins, followed by subjecting the attached cells to the hexosaminidase substrate as in Example 1–2. The results are given in FIG. 6.

Figure 6:
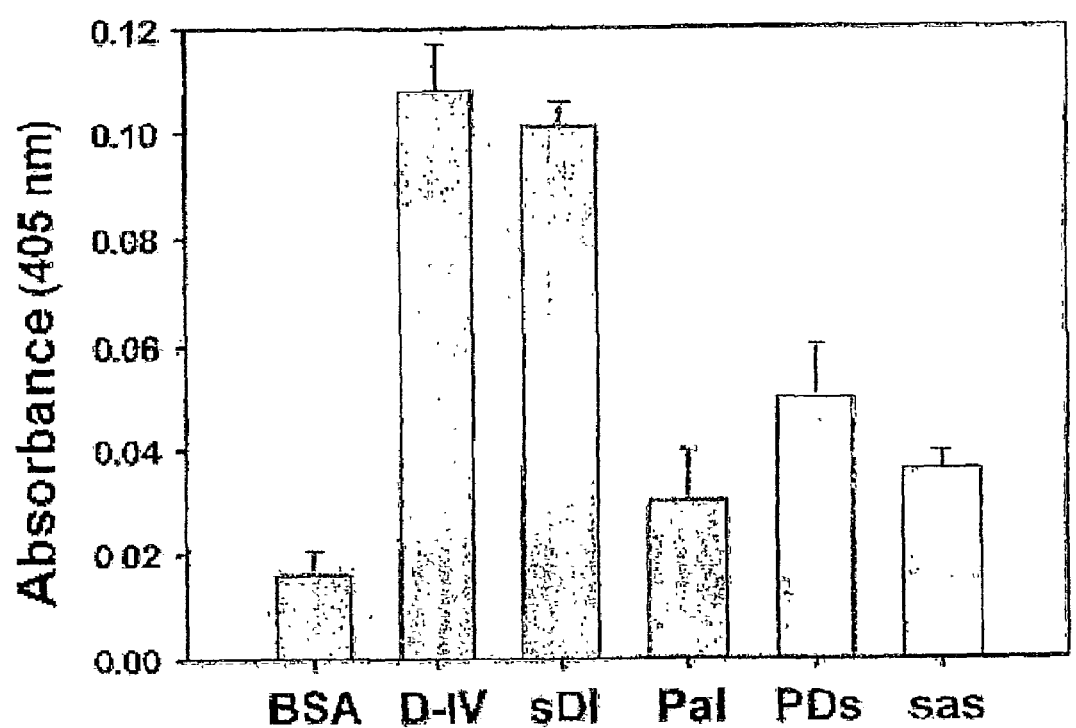
FIG. 6 is a histogram showing the cell attachment activity of substitution mutants derived from the $4^{th}$ fas-1 domain of βig-h3.

As seen in FIG. 6, the mutant protein having Ala instead of Asp617, named D617A (β igh3 D-IV-PaI) and the mutant protein having Ser instead of Ile618, named I618S (β igh3 D-IV-PDs) significantly blocked cell adhesion whereas the mutant protein having Ser instead of Pro616, named P616S (β igh3 D-IV-sDI) was found to show cell attachment activity comparable to that of the wild type control. As for the mutant protein in which the three amino acids were mutated, named P616S/D617A/I618S (β igh3 DIV-sas), its cell attachment activity was also far lower than the control.

The loss of the $1^{st}$ fas-1 domain-mediated cell attachment activity in the $1^{st}$ fas-1 domain mutated at Asp617 or Ile618 indicates that the aspartic acid at position 617 and isoleucine at position 618 are very important to mediate cell attachment activity of βig-h3.

These results agree with those of Example 1. Reviewing the results of Example 1, the aspartic acid and isoleucine, which are identified to be essential to mediate cell attachment activity, are conserved in both the $2^{nd}$ and $4^{th}$ fas-1 domains showing cell attachment activity, while only the aspartic acid is conserved in the $1^{st}$ fas-1 domain, which shows weak cell attachment activity. On the other hand, the $3^{rd}$ domain with no cell attachment activity has neither of the two amino acids. Consequently, the results taken together demonstrate that Asp617 and Ile618 are very important to mediate cell attachment and spreading activity of βig-h3.

Example 3

βig-h3-Mediated Synthetic Peptides with Cell Attachment, Spreading and Detachment Activity With the confirmation of the indispensability of aspartic acid and isoleucine for the cell attachment activity, peptides containing the two amino acids were synthesized and assayed for cell attachment and detachment activity.

3-1: Synthesis of βig-h3 fas-1 Domain-derived Proteins

Peptides derived from the $1^{st}$, $2^{nd}$ and $4^{th}$ fas-1 domains of βig-h3 and a control peptide were synthesized with the aid of an automated multiple peptide synthesizer (PE/ABD 433) by standard solid phase procedures and they were isolated and purified by reverse phase high performance liquid chromatography. The synthesized peptides were designed to have KADHH (a.a 219–223) of SEQ. ID. NO. 1, NKDIL (a.a. 354–358) of SEQ. ID. NO. 2, and EPDIM (a.a. 615–619) of SEQ. ID. NO. 3, corresponding to conserved sequences of the $1^{st}$, $2^{nd}$ and $4^{th}$ fas-1 domains of βig-h3, respectively, and the control peptide DEMPI had the same amino acid composition as the peptide EPDIM, but was changed in its amino acid sequence, as shown in FIG. 7.

3-2: Assay for Cell Attachment and Detachment Activity of Synthetic Peptides

Effect of the peptides containing conserved sequences of fas-1 domains of βig-h3 on βig-h3-mediated cell adhesion was examined with HCE cells. Cells were preincubated for 30 min in media containing 100 μM of each of the four synthetic peptides or no peptides and transferred to plastic culture dishes coated with 10 μg/ml BSA or 10 μg/ml βig-h3. The attached cells were subjected to quantitative hexosaminidase analysis as in Example 1–2. The results are given in FIG. 8a.

As shown in FIG. 8a, the synthetic peptides NKDIL and EPDIM, each containing both of the conversed aspartic acid-isoleucine residues, significantly blocked the HCE cell adhesion to βig-h3, showing excellent cell detachment activity, while the synthetic peptide KADHH containing only the conserved aspartic acid weakly inhibited the cell adhesion. On the other hand, the control peptide DEMPI containing neither of the conversed amino acid residues did not affect cell adhesion and thus had low cell detachment activity.

The HCE cell adhesion to the recombinant proteins βigh3 D-II and βigh3 D-IV was also examined in the presence or absence of the synthetic peptides. To this end, HCE cells were preincubated for 30 min in media containing 100 μM of each of the four synthetic peptides or no peptides and then transferred to plastic culture dishes coated with 10 μg/ml βigh3 D-II or D-IV. Following incubation, the attached cells were quantitatively analyzed with hexosaminidase as in Example 1–2. The results are shown in FIG. 8b.

As seen in FIG. 8b, blocking effects of the synthetic peptides obtained when the $2^{nd}$ and $4^{th}$ fas-1 domains were used as substrates were similar to those obtained when βig-h3 was used as a substrate.

3-3: Cell Adhesion of HCE Cells to Surfaces Coated with Synthetic Peptides

An experiment was carried out to determine whether each of the synthetic peptides is able to mediate cell adhesion. Well plates were coated with each peptide at concentrations of 0, 20, 40, 60, 80, 100 and 120 μM and then incubated with HCE cells at 37° C. for 1 hour. The attached cells were quantitatively analyzed with hexosaminidase as in Example 1–2. The results are shown in FIG. 9a.

The synthetic peptides NKDIL and EPDIM, each containing both aspartic acid and isoleucine, were found to mediate cell adhesion in dose-dependent manners. The synthetic peptide KADHH was also capable of mediating cell adhesion in a dose-dependent manner, but was low in activity compared to NKDIL and EPDIM. As expected, the control peptide having neither of the two amino acids was not active in cell adhesion.

3-4: Identification of Receptors for Mediating Cell Attachment, Spreading and Detachment Activity of Synthetic Peptides Function-blocking experiments using monoclonal antibodies against various integrin subunits were carried out to examine whether α3β1 integrin, known as a surface receptor of βig-h3, would be involved in the cell adhesion mediated by the synthetic peptides EPDIM and NKDIL. HCE was preincubated at 37° C. for 30 min in the presence of each of the monoclonal antibodies (5 μg/ml) against different types of integrins. The preincubated cells were transferred onto plates precoated with 100 μM EPDIM or 100 μM NKDIL and then incubated further at 37° C. for 1 hour, followed by the quantitative analysis with hexosaminidase substrate as in Example 1–2. The quantitative results are given in FIG. 9b.

As seen in FIG. 3, the $2^{nd}$ or $4^{th}$ fas-1 domain-mediated cell adhesion was almost completely inhibited by both antibodies against α3 and β1 integrin subunits. These results indicate that both the $2^{nd}$ and $4^{th}$ fas-1 domains are associated with α3β1 integrin to mediate cell adhesion.

3-5: Effect of Synthetic Peptides on Cell Adhesion to Various Extracellular Matrix Peptides To determine whether the inhibitory activity of synthetic peptides EPDIM and NKDIL against cell adhesion is specific to βig-h3, effects of the synthetic peptides on cell adhesion to various matrix proteins were examined. HCE cells were preincubated in media added with 100 μM of the synthetic peptide EPDIM or NKDIL or none of them and then applied to plates coated with various matrix proteins, including βig-h3, fibronectin, laminin, vitronectin, type I and type II collagen. After 1 hour of incubation, the attached cells were quantitatively analyzed with hexosaminidase as in Example 1–2. The results are shown in FIG. 10a.

As shown in FIG. 10a, the synthetic peptides NKDIL and EPDIM efficiently blocked cell adhesion not only to βig-h3 but also laminin, showing excellent cell detachment activity. However, they weakly inhibited cell adhesion to fibronectin and did not affect cell adhesion to type I and type II collagen and vitronectin at all. Accordingly, the results, taken together, suggest that the synthetic peptides NKDIL and EPDIM specifically compete with α3β1 integrin-interacting molecules.

Figure 10B:
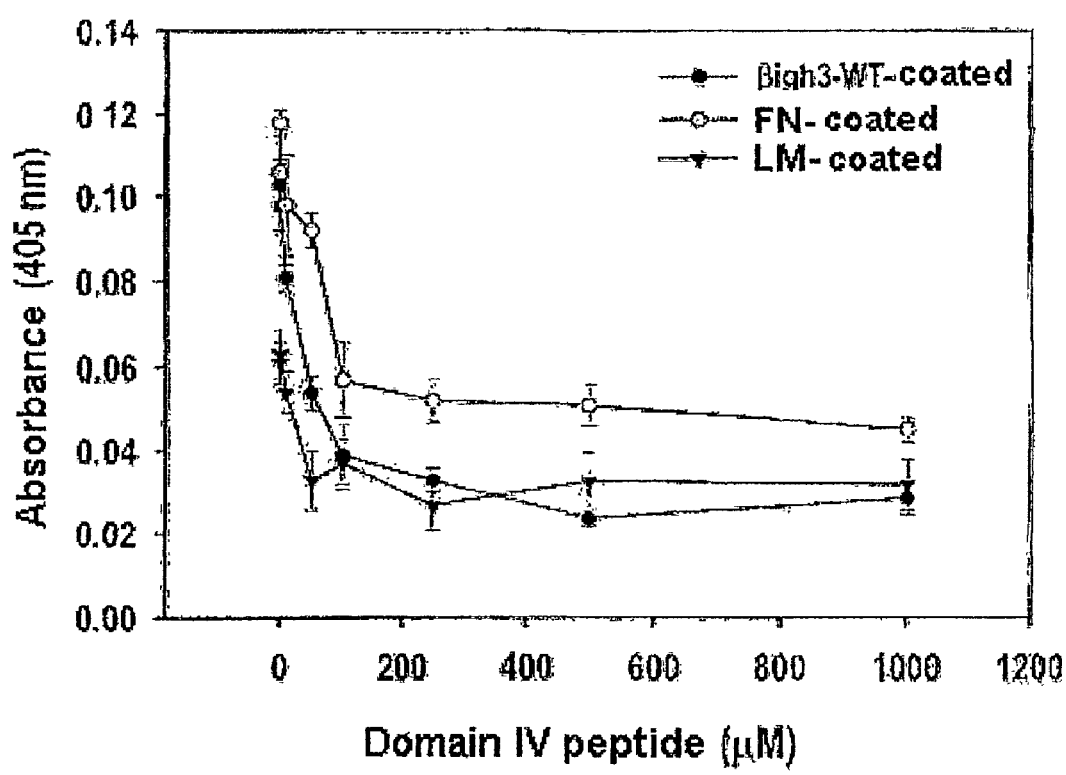
FIG. 10b is a curve showing dose-dependent inhibition of HCE cell adhesion surfaced coated with extracellular matrix proteins in the presence of various concentrations of EPDIM.

Cell adhesion to βig-h3, laminin and fibronectin, which was found to be blocked by the synthetic peptides NKDIL and EPDIM, was examined at various concentrations of EPDIM. HCE cells were incubated in media containing the synthetic peptide EPDIM at concentrations of 0, 200, 400, 600, 800, 1,000 and 1,200 μM and applied to plates coated with βig-h3, fibronectin and laminin. Following incubation for 1 hour, the attached cells were quantitatively analyzed with hexosaminidase as in Example 1–2. The results are shown in FIG. 10b.

As seen in the curves, the cell adhesion to βig-h3, fibronectin and laminin became weak as the concentration of the synthetic peptide EPDIM increased. That is, the inhibitory effects of EPDIM on cell adhesion to βig-h3, fibronectin and laminin were dose-dependent.

In the present invention, as described above, there are prepared the synthetic peptides NKDIL and EPDIM, both containing aspartic acid and isoleucine essential for cell attachment and spreading activity in their conserved motifs. The peptides contain conserved sequences of the $2^{nd}$ and $4^{th}$ fas-1 domains of βig-h3, each domain found to show cell attachment activity, and they induce cell adhesion through α3β1 integrin, known as a functional cell receptor. In the case of various extracellular matrix proteins known to bind to α3β1 integrin, such as thrombospondin, laminin, collagen type IV, etc., neither characteristic sequences having homology among their active sites, nor characteristic conserved binding motifs for α3β1 integrin have been discovered, thus far. However, given that the synthetic peptides NKDIL and EPDIM, each containing both the conserved amino acids aspartic acid-isoleucine, bind specifically to α3β1 integrin so as to mediate cell attachment activity, the conserved aspartic acid-isoleucine is identified as the characteristic conserved binding motif for α3β1 integrin in accordance with the present invention. Therefore, the peptides of the present invention can be usefully used for studying cell attachment activity mediated through various extracellular matrix proteins, including βig-h3, and for developing cell attachment, spreading and detachment-promoting peptides.

INDUSTRIAL APPLICABILITY

In accordance with the present invention, it is disclosed that, among four fas-1 domains of βig-h3, which is a cell adhesion molecule, the $2^{nd}$ and $4^{th}$ domains show cell attachment and detachment activity, and each have a conserved aspartic acid-isoleucine sequence, essential for the cell attachment and detachment activity. Given these findings, there are prepared peptides NKDIL and EPDIM, which contain the functional amino acid residues and induce cell adhesion through α3β1 integrin. The peptides of the present invention can be usefully used for studying cell attachment activity mediated through various extracellular matrix proteins, including βig-h3, and for developing cell attachment, spreading and detachment-promoting peptides.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A peptide having cell attachment, spreading and detachment activity consisting of EPDIM (SEQ ID NO:3).

2. The peptide according to claim 1, wherein the peptide mediates cell attachment and spreading activity through α3β1 integrin.

3. The peptide according to claim 1, wherein the peptide shows inhibitory activity against cell adhesion to βig-h3, fibronectin or laminin.

4. A pharmaceutical composition comprising the peptide of claim 1 as an active ingredient.

5. The pharmaceutical composition according to claim 4, wherein the pharmaceutical composition is therapeutically effective for wound healing, tissue regeneration, cancer metastasis resistance or improving biointerface of biomaterials and tissue implants.

6. A pharmaceutical composition for wound healing comprising the peptide of claim 1 as an active ingredient.

7. A pharmaceutical composition for inhibiting metastasis of cancer comprising the peptide of claim 1 as an active ingredient.

8. A pharmaceutical composition for tissue regeneration comprising the peptide of claim 1 as an active ingredient.

9. A pharmaceutical composition for improving biointerface of biomaterials and tissue implants comprising the peptide of claim 1 as an active ingredient.

* * * * *

SEQUENCE LISTING

```
<160> NUMBER OF SEQ ID NOS: 4
<210> SEQ ID NO 1
<211> LENGTH: 5
<212> TYPE: PRT
<213> ORGANISM: Homo sapiens

<400> SEQUENCE: 1

Lys Ala Asp His His
1               5

<210> SEQ ID NO 2
<211> LENGTH: 5
<212> TYPE: PRT
<213> ORGANISM: Homo sapiens

<400> SEQUENCE: 2

Asn Lys Asp Ile Leu
1               5

<210> SEQ ID NO 3
<211> LENGTH: 5
<212> TYPE: PRT
<213> ORGANISM: Homo sapiens

<400> SEQUENCE: 3

Glu Pro Asp Ile Met
1               5

<210> SEQ ID NO 4
<211> LENGTH: 5
<212> TYPE: PRT
<213> ORGANISM: Homo sapiens

<400> SEQUENCE: 4

Asp Glu Met Pro Ile
1               5
```